United States Patent [19]
Charney et al.

[11] Patent Number: 4,476,731
[45] Date of Patent: Oct. 16, 1984

[54] INJECTION VALVE FOR LIQUID CHROMATOGRAPHIC COLUMN AND SYSTEM THEREFOR

[75] Inventors: Andrew R. Charney, Bellefonte; Paul W. Kercher, Pennsylvania Furnace; William America, State College, all of Pa.

[73] Assignee: Scientific Systems, Inc., State College, Pa.

[21] Appl. No.: 471,473

[22] Filed: Mar. 3, 1983

[51] Int. Cl.³ .............................................. G01N 1/10
[52] U.S. Cl. ................................ 73/863.73; 231/149; 73/864.83
[58] Field of Search ........... 73/863.73, 863.72, 863.71, 73/864.84, 864.83; 251/149, 149.8, 149.9, 142

[56] References Cited
U.S. PATENT DOCUMENTS 3,114,393 12/1963 Vlasic ............................ 73/863.73 X
4,059,009 11/1977 Ball et al. ........................ 73/864.83
4,068,528 1/1978 Gundelfinger ................... 73/864.84
4,152,391 5/1979 Cabrera ....................... 73/864.83 X

FOREIGN PATENT DOCUMENTS 2028276 3/1980 United Kingdom ............. 73/863.72

Primary Examiner—S. Clement Swisher
Assistant Examiner—Tom Noland
Attorney, Agent, or Firm—Eric P. Schellin

[57] ABSTRACT

A multi-position rotary valve for injecting a variable liquid sample into a stream of diluent flowing through a high pressure liquid chromatograhic column, without interrupting diluent pressure conditions is disclosed. The valve is switchable between a load position and an inject position. Associated with the valve are a plurality of sample loops each of whose upstream ends are selectively connected to a needle cavity in the valve. Moreover the valve possesses means for arcuately articulation whereby one of the loops may be selected from loading of the sample and then for presentation to a diluent under pressure while in each of such position is also in operative alignment with the column.

9 Claims, 14 Drawing Figures

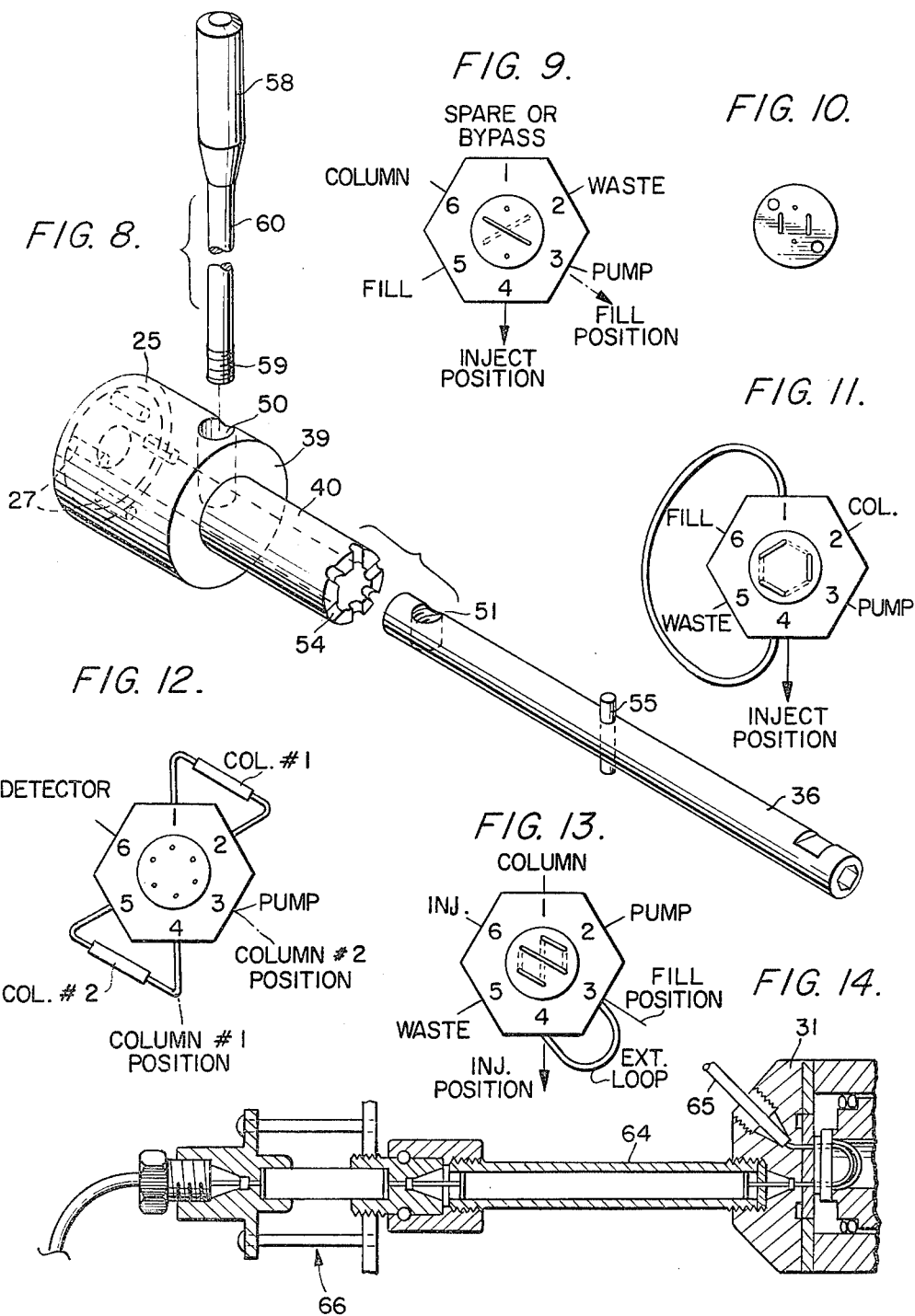

INJECTION VALVE FOR LIQUID CHROMATOGRAPHIC COLUMN AND SYSTEM THEREFOR

BACKGROUND OF THE INVENTION

1. Field of the Invention

The present invention generally relates to a valve for injecting a sample into a flowing stream and, more particularly, to a multi-position rotary valve for injecting a liquid sample into a high pressure stream of liquid by means of a conventional low pressure volumetric syringe without loss of sample and in a quantity which is quantitatively one of three.

2. Description of the Prior Art

In the field of liquid chromatography, the contents of a liquid sample, which consists of unknown quantities of compounds, is analyzed by injecting the sample in a stream of a suitable eluting solvent diluent, which passes through the chromatographic column and therefrom to an approprite detector. Typically, the solvent from an appropriate source is pumped to the column by a pump, e.g., a constant flow pump. Modern columns generate relatively high back pressures under normal operation, e.g. 2000 psi and above.

For many years the fixed loop sample injection valve has been used in high pressure liquid chromatography because of its convenience of use, reliablity and precision. Its major disadvantages are that a considerable amount of sample is wasted in the process of loading to insure that the sample loop is completely filled. Also, sample size can be changed only by changing the loop size. Syringe injection methods have been employed to circumvent these problems but not as satisfactorily as is now demonstrated in the present invention.

SUMMARY OF THE INVENTION

There is disclosed in the following an integrated sample injection valve and high pressure liquid chromatographic column system that requires no interconnecting tubing which causes peak broadening and that can be employed together for maximum efficiency. The injection valve and liquid chromatographic column can also be used separately with high efficiency and maximum versatility.

The liquid chromatrographic column is the subject of a U.S. patent application Ser. No. 328,907, filed Dec. 9, 1981, and now U.S. Pat. No. 4,389,313 entitled: Chromatographic Column with Improved Seals. The subject matter of the application is incorporated herein by reference.

The system includes an injection valve and liquid chromatographic column which is capable of communicating directly without tubing; without severely angled paths that decrease efficiency and increases peak broadening and with minimum dispersion volume between the sample loop, column and detector.

The injection valve includes a rotor with a stator disc. A passage in the stator is provided adapted and constructed to receive a ferrule for syringe needle that can transfer the sample through the stator into one of the aligned loops in the rotor and which is vented to waste during delivery of the sample to a loop. The rotor of the valve is then rotated one-sixth of a turn to put the sample loop in series with the solvent input and the liquid chromatographic column.

The injection valve of the present invention has a rotor disc carrying three loops, each of which have differing lengths and/or internal diameters thereby providing the possibility of different volumes of sample in a single valve without disassembly and assembly. The present valve can change high efficiency internally positioned loops externally without disassembly and readjustment of valve to change loops.

A radially extending handle on the device of the present invention is unscrewed and the shaft of the rotor is rotated until the desired loop number appears in the handle window. A shaft of the rotor is then pulled back and rotated until the tapped hole of the shaft lines up with a window. The shaft is then pushed inwardly and the handle for the valve is then replaced.

BRIEF DESCRIPTION OF THE DRAWINGS

FIG. 8 is an exploded view of the rotor used in the valve;

FIG. 9 is a schematic view of the port positions.

FIG. 10 is a schematic view a loop carrying disc.

FIG. 11 is another embodiment of the invention.

FIG. 12 is still another embodiment of the invention;

FIG. 13 is yet another embodiment of the invention;

FIG. 14 is a cross-sectional view of a part of the valve of the present invention in direct association with a column chromatographic tube and a conventional photoelectric detector.

DETAILED DESCRIPTION OF THE INVENTION

Figure 1:
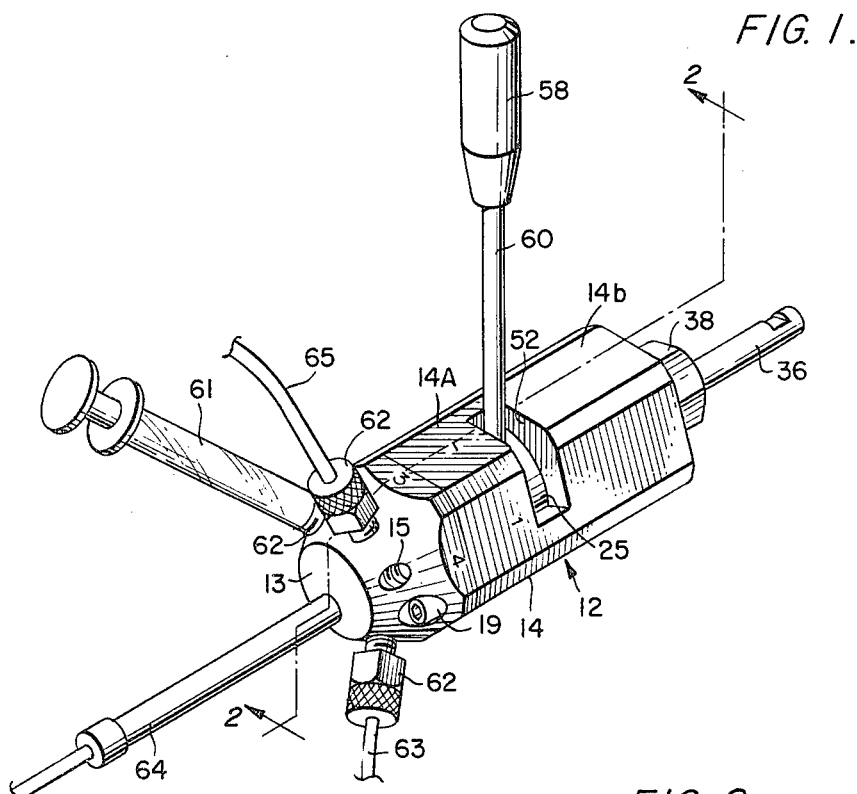
FIG. 1 is a perspective view of the injection valve of the present invention.
Figure 2:
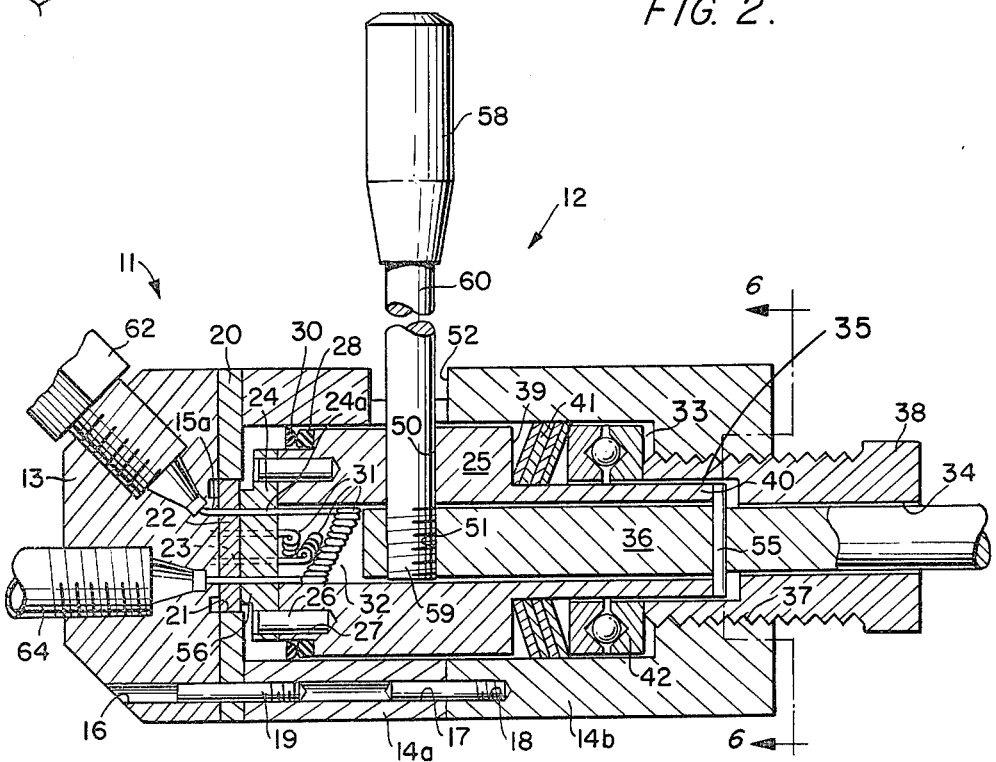
FIG. 2 is a cross-sectional view taken along line 2—2 of FIG. 1.
Figure 3:
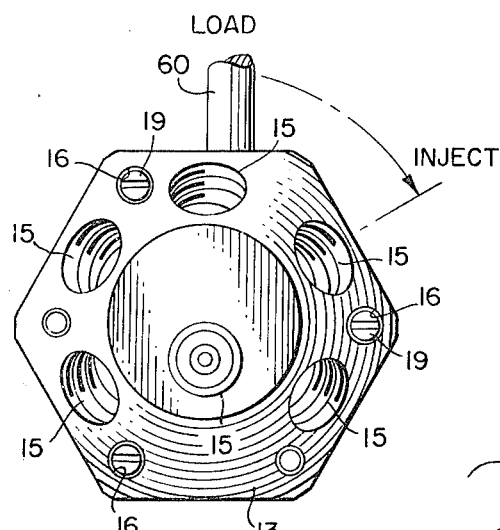
FIG. 3 is a front view of the valve of the present invention showing the various ports.
Figure 4:
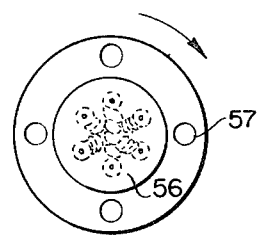
FIG. 4 is a rear view of the disc disassembled from the valve of the present invention.

Attention is now directed to the drawings, especially to FIGS. 1, 2 and 3 for detailed consideration of the ingenious design of the injection valve of the present invention. The valve body 11 consists essentially of a three part hexagonal stator structure 12 having a cap 13 and a hollow main body 14, which consists of a hollow forward part 14a and a hollow rearward part 14b. The cap 11 has a plurality of ports 15, preferably six in number, which can be readily seen in FIG. 3. Each of the ports have female threads to which ferrule containing conduits may be selectively attached for the purposes intended.

The cap 13 is bolted by means of three bolts to the rearward part 14b. Forward part 14a is sandwiched between cap 11 and rearward part 14b. From FIG. 3, it will be seen that three bolt receiving bores 16 are located in the cap 13 which are essentially equidistantly spaced about the cap 13. Each of the bores 15 is supplied with a machine screw 19 which pass through suitably aligned bores 17 in forward part 14a and terminated in female threaded receiving bores 18 in rearward part 14b.

The bottom portion of the cap 13 is fitted with a hexagonal ring 20 having an annular central opening 21. A stator disc 22 is positioned in the opening 21. It is contemplated that in one embodiment that the hexagonal ring 20 is machined as a part of the cap 13 and the opening 21 is simply an appropriately machined recess.

The stator disc 22 is supplied with six axially equidistantly bores 23 each of which is in communication with a respective single port 15 of the cap 13 through suitable passageways 15a. The stator disc may be constructed of a polymeric material.

A rotor disc 24 is positioned in confrontation with regard to the stator disc 22 at the side opposite to the passageways 15a to the ports 15 as mentioned immediately above. The rotor disc 24 has six axially equidistantly positioned bores 24a which are in alignment with the bores 23 of the stator disc 22. The rotor disc is mounted at one face end of rotor 25. The rotor disc 24 is held in place on the rotor 25 by alignment pins 26 which extent rearwardly from the rotor disc and sit in suitably disposed recess bores 27. The rotor is adapted and constructed to fit smoothly internally of said hollow forward parts 14a and said hollow rearward part 14b. A rotor seal 28 is positioned at the outer front face of the rotor 25 and is designed to retain a rotor back up ring 30.

Figure 7:
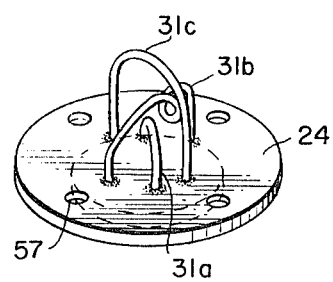
FIG. 7 is a perspective of the disc showing various loops.

The rotor disc 24 is supplied with three tubular loops 31 of varying lengths at the rearwardly facing part thereof. The ends of each tubular loop terminate at two of the bores in said rotor disc 24 whereby their respective ends are 180° apart. The rotor 25 is supplied with a cylindrical space 32 of sufficient volume to accommodate the aforementioned loops. Each of the loops is of a different length and/or internal diameter and thereby controls the volume of the sample to be injected into the liquid chromatographic column. It will be seen from the drawings that the loops are in the form of a helix to the degree necessary to accommodate their respective lengths. The perspective view of the rotor disc 24 as shown by FIG. 7 clearly demonstrate the structure of the various loops 31a, 31b and 31c.

The rotor 25 has a concentrically positioned bore 35 into which there is projected shaft 36. Shaft 36 extends rearwardly beyond the rearward part 14b through an axial large bore 37 having a female thread into which is screwed a coaxial nut 38 which has a bore 34 there through suitably dimensioned to accommodate the said shaft 36.

The rearward part 14b has a space 33 to accommodate the rearward portion of the rotor 25. The said rearward portion of the rotor has a shoulder portion 39 producing a diminished axially extending cylindrical portion 40. The shoulder portion has in confronting abutment there against a plurality of spring thrust washers 41 which are also concentric with regard to the said diminished axially extending cylindrical portion 40. At the opposite side of said plurality of thrust washers is a thrust bearing 42 mounted concentrically on said diminished axially extending cylindrical portion 40. It will be seen from FIG. 2 that the coaxial nut 38 is adapted and constructed to supply appropriate pressure against thrust bearing 42 which compresses the rotor 25, the rotor disc 24 against stator disc 22 to insure liquid tight communication between the bores terminating at the surface of the stator disc and the bores complementarily located at the surface of the rotor disc.

The rotor 25 has a radially positioned bore 50. The internal end portion of the shaft 36 has a female threaded bore 51 capable of being in alignment with the bore 50 of the rotor 25. Foreward part 14a is supplied with a slot 52 having an accuate dimension of at least 60° and is also in alignment with the aforementioned bores 50 and 51. A radially extending handle 60 having a male portion 59 at one end is screwably secured to the shaft 36 into female bore 51. The other side of the handle 60 terminates in a knob 58.

The most rearward end of the diminished axially extending cylindrical portion 40 is supplied with six radially extending slots 54 opening rearwardly. The six slots are equidistantly disposed whereby two slots of the six are always in radial alignment, thereby providing three alignments. A perpendicular pin 55 is located through the shaft 36. The pin 55 has that portion of the pin 55 extending from the shaft in position at two of the aligned slots.

It will be appreciated that appropriate aligning pins are provided whereby the components may be taken apart and reassembled without concern that the bores will not be properly aligned.

An ingenious advantage of the present invention is the fact that any one of the three loops may be selected for utilization. This is accomplished as can be seen from FIG. 8, for instance, where the shaft 36 is shown exploded from the rotor and the handle 60 is shown exploded from both the shaft 36 and the rotor 25.

FIG. 7 shows the rotor disc 24 from the side opposite to the side carrying the various loops so they are shown in dotted lines. A series of four alignment openings 57 will be noted, detailed to fit the pins 26 of the rotor as can be seen better from FIG. 2. It will also be noted that the rotor disc 24 has a raised central portion 56. The surface thereof is subject to excellent machining and being somewhat raised so that any protrusions of the alignment pins 26 are avoided.

While six ports 15 are shown in the cap 13, actually for most purposes only four ports are necessary. For instance as shown in FIG. 1, ferrule 62 is screwed into a port which for the purposes intended becomes the sample port as can be seen by the fact that a sample dispensing syringe 61 is in position. An elongated conduit 63 is at the bottom portion of the cap 13 and 180° distant from the sample port and the latter acts as a waste line.

The front facing port of the cap 13 is seen to have directly secured to it an elongated high pressure liquid chromatographic column 64. As has been detailed elsewhere herein there are advantages in making it possible for a direct connection between the injection valve of the present invention and the liquid chromatographic column of the invention as described in the aforementioned patent application. The said application also usefully discloses the cover ferrules and threaded ports associated therewith. At the top of the cap is another elongated conduit 65 which carries the conventional solvent for distribution to the column 64.

Figure 5:
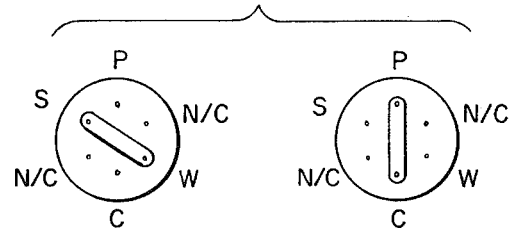
FIG. 5 is a schematic showing of a selection of loops.
Figure 6:
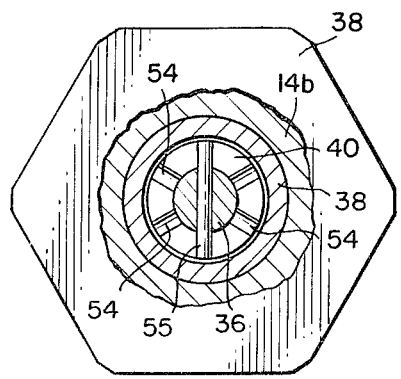
FIG. 6 is a cross-sectional view taken along line 6—6 of FIG. 2.

FIG. 5 shows load and inject schemata, in the same reference direction as whown by FIGS. 1 and 3. To the left of FIG. 5 the appropriately selected loop is ported at one end thereof to sample receiving position and the end is ported to waste. The handle 60 is as shown in the said Figures. When the sample has been injected the handle is moved arcuately clockwise 60° as shown by FIG. 3. This movement brings the ends of the same loop in series between the "P" or solvent under pressure port as supplied by the conduit 65. The other end of the sample carrying loop is ported to the column. 64.

The ports 15 are each coned inwardly and the various ferrules used are appropriately complementary to insure excellent centering of the terminus of each ferrule in direct alignment with its appropriate passageway 15a.

The high efficiency valve configuration can be changed to accommodate an external bypass loop by changing the standard stator disc to one which connects ports 1 & 6 and 3 & 4 together and connecting the proper length and internal diameter tube to ports 1 & 4 which allows flow during the time that the ports are cut-off during actuation. See FIG. 10 for a very schematic approach.

Attention is directed to FIG. 11 for a loop rotor disc jumpered externally for large volume external loop injector, for instance for prior preparation and loading of the system. In FIG. 12 one can see such uses as a liquid chromatographic column selection.

A loop disc jumpered as per FIG. 13 can be used as a partial fill or fully filled loop with negligible sample loss as there is injection into the front position.

FIG. 14 depicts the use of the injection valve of the present invention in fragmentary form in operative association with a liquid chromatographic column 64 as shown and disclosed in the aforementioned patent application. The terminus of the said column 64 is to a conventional photoelectric detector 66 for analyzing purposes as is accomplished.

It will be noted that maximum utilization of the design is achieved by primarily three unique contributions. In first consideration, it is noted that the contents of the sample loop may be transferred directly to the column through an aligned egress liquid chromatographic column egress port. With the heretofore mentioned valve in the load position a syringe bearing sample is used to fill one of the sample loops. Provision is made whereby any excess sample drains to waste. The radially extending handle is shifted 60° clockwise by manual or by remotely controlled mechanical driving means thereby repositioning the filled sample loop between the pressurized solvent carrying line and the liquid chromatographic column to thereby deliver the sample straight to the column. The liquid chromatographic column which is the subject of the aforementioned U.S. patent application can be used with the said injection valve providing for minimum bandspreading by diminishing volume and coupling directly to the column.

Extremely small sample loop sizes are available. As was noted during the extensive discussion in the above, there are three different loop sizes available on each rotor disc. Sample loop size is selected by indexing the rotor 25 and its rotor disc 24 without the need for disassembly. In order to change the loop size, the valve handle 60 is unscrewed and removed from the rotor allowing the shaft 36 to be slightly retracted. The indexing pin 55 is turned with the rotation of the freed shaft 36 and is placed in the desired index slot pair 54 at the rear of the rotor 25. The shaft is turned until the appropiate rotor handle hole becomes accessible through the hexagonal stator. The handle is then screwed back into the rotor and into shaft hole 51 as before. It will be appreciated that the entire rotor disc can be changed simply by the removal of the stator, cap, its associated disc and its retainer disc and replaced with a rotor disc of an entirely different configuration.

As there is abutting movement everytime the valve is filled or loaded and then moved to the inject position, of considerable importance to the carrying out of the invention is the fact that the surface carrying the bore openings on the cap 13 and the bore openings on the rotor disc 24 carrying the loops have interposed therebetween a stator disc 22 made of a polymeric material which with first signs of wear is easily replaceable. Many materials are conventional for this purpose. Of primary importance is the fact that stator disc 22 should be of considerably less hardness than the opposing surfaces of the cap 13 and the rotor disc, especially the latter because it is at that interface that the sliding motion will occur between the fill and the inject position.

The loops are brazed onto the rotor disc. The space provided for the loops in the rotor 25 is sufficient for three sample loops which can vary anywhere from 0.1 ul to 10 ul capacity.

The injection valve of the present invention can be connected by suitable tubing to any liquid chromatographic column. The shaft 36 at the rear end portion can be the means for motorized actuation when desired.

What is claimed is:

1. An injection valve system for liquid chromatographic columns comprising a valve body, said valve body having in axial alignment a cap, a stator, a rotor and an indexing shaft, said cap comprising a forward end of said stator, said cap having a plurality of ports each of said ports having a passageway in the direction axially of the said stator and each terminating in a flat portion of the cap, said rotor located internally of said stator, said rotor being open in the direction of said cap and said cap closing said opening when said cap and said stator is assembled, said rotor having an axial concentric bore, a disc closing off the bore of the rotor at the portion thereof facing the cap, said disc having a plurality of bores in axial alignment with the bores of the cap terminating at said flat portion thereof, said disc having a plurality of conduits mounted on the portion of the disc that faces the open interior of said rotor, each of said conduits having one end terminating at one of said bores of said disc and its other end terminating at one other of said bores, a stator disc positioned between said cap at the flat portion thereof and the said disc against the surface opposite to the one having said conduits, said stator disc having a plurality of axially disposed bores in alignment with the bores of said flat portion of the cap and the bores of said rotor mounted disc, means mounted between said rotor and a rearward end of said stator to retain said stator disc in its position, removable means for rotating said rotor and said disc carrying said conduits whereby to alter the bores of the said disc with respect of said bores of said stator disc during which one preselected conduit is in operative position, means for further indexing into operative position a different conduit and taking out of operative position a first selected conduit when said removable means has been removed.

2. The injection valve of claim 1 wherein the stator is constructed of at least two axially aligned separable parts.

3. The injection valve of claim 2 wherein the stator disc is constructed of a material having a hardness less than at least the surface of the disc carrying the conduits on that side thereof facing said stator disc.

4. The injection valve of claim 3 wherein said stator has a radial slot and said removable means includes a handle extending radially through said slot, having one end thereof operatively associated with said rotor.

5. The injection valve of claim 4 wherein said means for indexing includes in the bore of said rotor a shaft extending axially outwardly in a direction opposite to the said disc carrying said conduits and rearwardly beyond said stator, said handle being removably connected to an end portion of said shaft, said shaft having a plurality of engaging means and said rotor having complementary engaging means each adapted and constructed to be operative with each when said handle is removed whereby the engaging means of said shaft may be brought into selective engagement with said rotor to arcuately index said rotor.

6. An injection valve system for liquid chromatographic columns comprising a valve body, said valve body having in axial alignment a cap, a stator, a rotor and an indexing shaft, said cap comprising a forward end of said stator, said cap having a plurality of ports each of said ports having a passageway in the direction axially of the said stator and each terminating in a flat portion of the cap, said rotor located internally of said stator, said rotor being open in the direction of said cap and said cap closing said opening in the rotor when said cap and stator is assembled, said rotor having an axial concentric bore, a disc closing off the bore of the rotor at the portion thereof facing the cap, said disc having a plurality of bores in axial alignment with the bores of the cap terminating at said flat portion thereof, said disc having a plurality of conduits mounted on the portion of the disc that faces the open interior of said rotor, each of said conduits having one end terminating at one of said bores of said disc and its other end terminating at one other of said bores, a stator disc positioned between said cap at the flat portion thereof and the said disc against the surface opposite to the one having said conduits, said stator disc having a plurality of axially disposed bores in alignment with the bores of said flat portion of the cap and the bores of said rotor mounted disc, means mounted between said rotor and a rearward end of said stator to retain said stator disc in its position, removable means for rotating said rotor and said disc carrying said conduits whereby to alter the bores of the said disc with respect of said bores of said stator disc during which one preselected conduit is in operative position, means for further indexing into operative position a different conduit and taking out of operative position a first selected conduit when said removable menas has been removed, at least one of said ports of said cap being in operative association with one end of a liquid chromatographic column.

7. The system of claim 6 wherein at least one port of said cap is in direct axial alignment with a bore of the stator disc and of the disc carrying the said conduits whereby fluid flowing from an end of said conduit is capable of flowing without turns and a receiving end of said liquid chromatographic column is mounted directly to said port of said cap which is in direct axial alignment.

8. The system of claim 7 wherein detector means is mounted at the other end of said liquid chromatographic column.

9. The system of claim 6 wherein detector means is mounted at the other end of said liquid chromatographic column.

* * * * *